US00PP19600P2

(12) United States Plant Patent
Verschoor

(10) Patent No.: US PP19,600 P2
(45) Date of Patent: Dec. 30, 2008

(54) ***PHLOX* PLANT NAMED 'FONDANT FANCY'**

(50) Latin Name: *Phlox paniculata*
Varietal Denomination: Fondant Fancy

(75) Inventor: Jan Verschoor, Haarlem (NL)

(73) Assignee: Witteman & Co, Hillegom (NL)

( * ) Notice: Subject to any disclaimer, the term of this patent is extended or adjusted under 35 U.S.C. 154(b) by 0 days.

(21) Appl. No.: 11/998,935

(22) Filed: Dec. 3, 2007

(51) Int. Cl.
*A01H 5/00* (2006.01)

(52) U.S. Cl. ..... Plt./320
(58) Field of Classification Search ..... Plt./320
See application file for complete search history.

*Primary Examiner*—Annette H Para
*Assistant Examiner*—Georgia Helmer
(74) *Attorney, Agent, or Firm*—Jondle & Associates, P.C.

(57) ABSTRACT

A new *phlox* plant particularly distinguished by soft pink flowers with darker eyes, compact plant habit, healthy foliage and good mildew resistance is disclosed.

2 Drawing Sheets

Genus and species: *Phlox paniculata.*
Variety denomination: 'Fondant Fancy'.

BACKGROUND OF THE NEW PLANT

The present invention comprises a new and distinct cultivar of *phlox,* botanically known as *Phlox paniculata,* and hereinafter referred to by the cultivar name 'Fondant Fancy'. The new cultivar originated from an open pollination in 2004 in Haarlem, The Netherlands between unknown male and female *Phlox paniculata* plants.

The new cultivar was selected in 2005 from the results of the open pollination in Haarlem, The Netherlands and has been asexually reproduced through multiple generations by vegetative cuttings in Haarlem, The Netherlands since that time. The present invention has been found to retain its distinctive characteristics through successive asexual propagations.

Plant Breeder's Rights for this cultivar were applied for in the European Union on Feb. 16, 2006. 'Fondany Fancy' has not been made publicly available more than one year prior to filing of this application.

SUMMARY OF THE INVENTION

The following are the most outstanding and distinguishing characteristics of this new cultivar when grown under normal horticultural practices in Haarlem, The Netherlands.

1. Soft pink flowers with dark eyes;
2. Compact habit;
3. Healthy foliage; and
4. Good mildew resistance.

DESCRIPTION OF PHOTOGRAPHS

This new *phlox* plant is illustrated by the accompanying photographs which show blooms and foliage of the plant in full color, the colors shown being as true as can be reasonably obtained by conventional photographic procedures. The photographs are of a 2-year-old plant grown outdoors in Haarlem, The Netherlands.

DESCRIPTION OF THE NEW CULTIVAR

Figure 1:
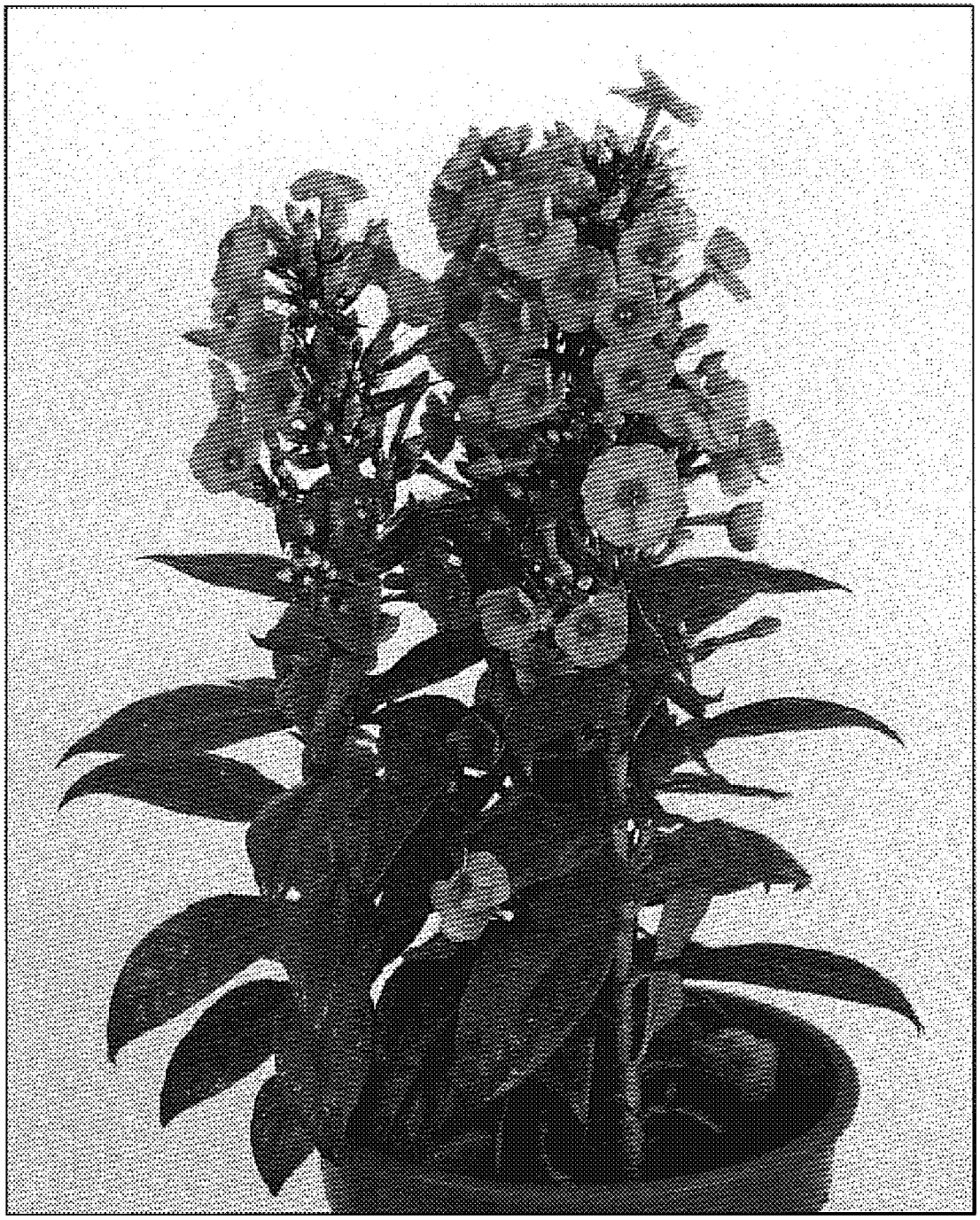
FIG. 1 shows the overall plant habit, including blooms, buds and foliage.
Figure 2:
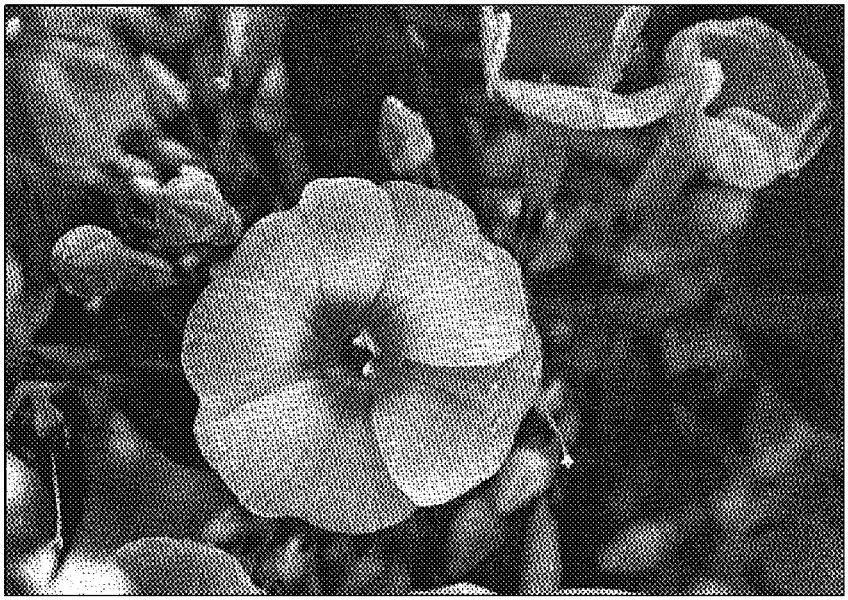
FIG. 2 shows flower buds and mature flowers.
Figure 3:
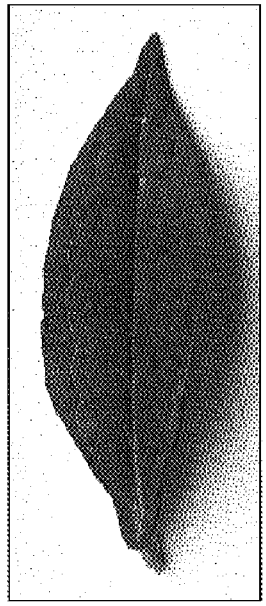
FIG. 3 shows a mature leaf of the plant.

The following detailed description sets forth the distinctive characteristics of 'Fondant Fancy'. The data which define these characteristics were collected from asexual reproductions carried out in Haarlem, The Netherlands. The plant history was taken in September on 2-year-old plants which were planted and grown outdoors in daytime temperatures between 13° C. and 27° C. and nighttime temperatures between 4° C. and 14° C. No pinchings, growth retardants or photoperiodic treatments were used. Observations were made when the plants were in natural outdoor light. Color references are primarily to the R.H.S. Colour Chart of The Royal Horticultural Society of London (R.H.S.) (2001).

DETAILED BOTANICAL DESCRIPTION

Classification:
- *Family.*—Polemoniaceae.
- *Botanical.—Phlox paniculata.*
- *Common name.—Phlox.*

Parentage:
- *Female parent.*—Unknown individual plant of *Phlox paniculata.*
- *Male parent.*—Unknown individual plant of *Phlox paniculata.*

Growth:
- *Form.*—Herbaceous perennial.
- *Habit.*—Upright, low to moderate vigor.
- *Shape.*—Columnar.
- *Height (measured from the top of the soil).*—35.6 cm.
- *Diameter*—24.9 cm.
- Growth rate.—10.0 cm per month.
- *Flowering response.*—9 months.
- *Time to produce a finished flowering plant.*—25 weeks from rooted cutting for a 1.5 liter container.
- *High temperature tolerance.*—Tolerant to at least 35° C.
- *Lower temperature tolerance.*—Hardy to USDA Zone 6.

*Roots.*—Fine white, sparse, freely branching; approximately 30 days for rooting.

Branches:

*Habit.*—Moderate basal branching, flowering stems grow from base.

*Number of branches.*—3 flowering stems.

Stems:

*Description..*—Round, glaborous, slightly glossy.

*Aspect.*—Rounded.

*Color.*—RHS 144A (Yellow-green).

*Diameter.*—0.5 cm.

*Stem length* (*excluding inflorescence*).—17.1 cm.

*Internode length.*—1.9 cm.

*Strength.*—Strong.

*Pubescence.*—Absent.

Leaves:

*Arrangement.*—Opposite, single.

*Quantity of leaves* (*per lateral branch*).—20.

*Durability to stress.*—High.

*Shape.*—Elliptic.

*Apex.*—Long apiculate.

*Base.*—Obtuse.

*Color* (*mature leaves*).—Upper surface: RHS 137A (Green) to RHS 139A (Green). Lower surface: RHS 137C (Green).

*Color* (*immature leaves*).—Upper surface: RHS 141A (Yellow-green). Lower surface: RHS 137C (Yellow-green).

*Margin.*—Slightly revolute, very short, fine serration (approx. 30 teeth per cm).

*Size.*—Length: 10.0 cm. Width: 3.5 cm.

*Texture.*—Smooth, glabrous.

*Pubescence.*—Absent.

*Venation.*—Type: Pinnate. Color: Upper surface: RHS 144A (Yellow-green). Lower surface: RHS 144B (Yellow-green).

*Petiole.*—Shape: V-shaped. Length: 0.5 cm. Width: 0.3 cm. Height: 0.3 cm. Color (Both surfaces): RHS 144A (Yellow-green) to RHS 144B (Yellow-green).

Flower buds:

*Color.*—RHS 72B (Red-purple), lower half (immature calyx) RHS N186C (Greyed-purple) with an RHS 145A base (Yellow-green).

*Shape.*—Obovate.

*Size.*—Length: 1.9 cm. Diameter 0.5 cm.

*Rate of opening.*—Open approximately 4 days from stage described above.

Inflorescence:

*Blooming habit: Continuous once a year.*

*Inflorescence type.*—Self-cleaning, compound terminal panicle.

*Natural flowering season.*—Summer to late summer (July to late September).

*Height.*—18.5 cm.

*Width.*—10.6 cm.

*Fragrance.*—Low, sweet; typical *Phlox paniculata* scent.

*Flower number* (*per inflorescence*).—200.

*Quantity of flowers per lateral stem.*—30.

*Quantity of flower buds per lateral stem.*—170.

*Quantity of flower and buds per plant.*—600.

*Rate of flower opening.*—Approximately 15% of the flowers at any stage.

*Flower longevity on plant.*—10 days.

*Flower longevity as a cut flower.*—10 days.

Peduncle:

*Color.*—RHS 144A (Yellow-green) to RHS 144B (Yellow-green).

*Length.*—Primary: 14.7 cm. Secondary: 3.9 cm.

*Diameter.*—Primary: 0.3 cm. Secondary: 0.15 cm.

*Angle.*—Primary peduncles average angle 0° (straight upright), secondary peduncles with an average angle of 35°.

*Strength.*—Strong.

Pedicel:

*Color.*—RHS 144A (Yellow-green) to RHS 144B (Yellow-green).

*Length.*—0.4 cm.

*Diameter.*—0.1 cm.

*Angle.*—Average angle 30° (0° to 60°) (0°=straight on top of the peduncle).

*Strength.*—Strong.

Florets:

*Type.*—Single.

*Shape.*—Salverform.

*Aspect.*—Upright and outward.

*Fragrance.*—Moderate, sweet; typical *Phlox paniculata* scent.

*Size.*—Height (flower depth): 2.5 cm. Diameter: 3.1 cm.

*Petals.*—Arrangement: Rotate. Shape: Spathulate, the lower 60% fused into a tube. Appearance: Dull, smooth. Number: 5, fused into a tube (lower 60% of each petal). Size: Length: 3.6 cm (lower 2.1 cm fused into a tube). Width: 1.9 cm. Apex: Rounded. Margin: Entire. Color (when opening): Upper surface: RHS 77B (Purple) to RHS 77C (Purple), base of free part RHS N74A (Red-purple), tube RHS N77D (Purple) but slightly lighter. Lower surface: RHS 76A (Purple), tube RHS N77B (Purple). Color (fully opened): Upper surface: RHS N80D (Purple-violet), base of free part RHS N74B (Red-purple), tube RHS N77D (Purple) but slightly lighter. Lower surface: RHS 76B (Purple), tube RHS N77B (Purple). Color fading to: RHS N82D (Purple-violet). Texture (both surfaces): Smooth.

Calyx:

*Shape.*—Campanulate.

*Length.*—0.9 cm.

*Diameter.*—0.35 cm.

*Sepals.*—Arrangement: Rotate. Appearance: Smooth, dull. Number: 5. Shape: Linear. Apex: Narrow apiculate. Base: Lower 25% fused. Margin: Entire. Size: Length: 0.9 cm. Width: 0.2 cm. Color (mature): Both surfaces: RHS N186C (Greyed-purple) with an RHS 144A (Yellow-green) to RHS 144B (Yellow-green) base. Color (immature): Both surfaces: RHS N186C (Greyed-purple) with an RHS 145A (Yellow-green) base.

Reproductive organs:

*Stamens.*—Quantity: 5.

*Anther.*—Shape: Basifixed, oblong; filament implanted in petal. Length: 0.25 cm. Length of filament: 0.1 cm. Color RHS 155C (White).

*Pollen.*—Amount: Low. Color: RHS 4D (Yellow).

*Pistil.*—Quantity: 1. Length: 1.8 cm.

*Style.*—Length: 1.7 cm. Color: RHS 146C (Yellow-green) flushed with RHS N77C (Purple).

*Stigma.*—Shape: Cleft (3-parted). Color: RHS 150C (Yellow-green).

*Ovary color.*—RHS 143A (Green).

Fruit and seed set: No fruit or seeds detected to date.

Disease and insect resistance: No particular resistance or susceptibility to diseases or insects noted to date.

COMPARISON WITH PARENTAL AND COMMERCIAL CULTIVARS

'Fondant Fancy' differs from the commercial *Phlox paniculata* variety 'Bright Eyes' (unpatented), by having darker, healthier foliage with thicker stems and a sturdier plant habit than 'Bright Eyes'. Additionally, 'Fondant Fancy' has a more compact plant habit and a deeper, dark pink flower color than 'Bright Eyes'.

'Fondant Fancy' differs from the commercial *Phlox* variety 'Grenadine Dream' (U.S. Plant patent application Ser. No. 11/725,797), by having soft-pink flower with darker eyes while 'Grenadine Dream' has rich red-purple flowers.

I claim:

1. A new and distinct cultivar of *Phlox* plant as shown and described herein.

* * * * *